US012611250B2

(12) United States Patent
Hancock et al.

(10) Patent No.:  US 12,611,250 B2
(45) Date of Patent:      Apr. 28, 2026

(54) ELECTROSURGICAL SYSTEM FOR IDENTIFYING AND TREATING BIOLOGICAL TISSUE

(71) Applicant: Creo Medical Limited, Chepstow (GB)

(72) Inventors: Christopher Paul Hancock, Chepstow (GB); John Bishop, Chepstow (GB); George Hodgkins, Chepstow (GB)

(73) Assignee: Creo Medical Limited, Chepstow (GB)

( * ) Notice: Subject to any disclaimer, the term of this patent is extended or adjusted under 35 U.S.C. 154(b) by 0 days.

(21) Appl. No.: 19/170,833

(22) Filed: Apr. 4, 2025

(65) Prior Publication Data

US 2025/0281236 A1      Sep. 11, 2025

Related U.S. Application Data

(63) Continuation of application No. 18/709,737, filed as application No. PCT/EP2022/079248 on Oct. 20, 2022, now Pat. No. 12,268,442.

(30) Foreign Application Priority Data

Dec. 15, 2021      (GB) ..................................... 2118160

(51) Int. Cl.
    *A61B 18/12*          (2006.01)
    *A61B 18/18*          (2006.01)
    *A61B 18/00*          (2006.01)
(52) U.S. Cl.
    CPC   *A61B 18/1815* (2013.01); *A61B 2018/00172* (2013.01); *A61B 2018/00577* (2013.01);
                        (Continued)
(58) Field of Classification Search
    CPC . A61B 18/1815; A61B 18/12; A61B 18/1206; A61B 18/18; A61B 18/1233;
                        (Continued)

(56) References Cited

U.S. PATENT DOCUMENTS

| | | | |
|---|---|---|---|
| 2009/0192441 A1 | 7/2009 | Gelbart et al. | |
| 2010/0030207 A1* | 2/2010 | Hancock | A61B 18/1815 |
| | | | 606/33 |

(Continued)

FOREIGN PATENT DOCUMENTS

| | | |
|---|---|---|
| WO | 2018087601 A1 | 5/2018 |
| WO | 2018200865 A1 | 11/2018 |
| WO | 2020221485 A1 | 11/2020 |

OTHER PUBLICATIONS

International Search Report and Written Opinion, issued by the International Searching Authority in corresponding International Patent Application No. PCT/EP2022/079248, dated Feb. 21, 2023.

(Continued)

*Primary Examiner* — Thomas A Giuliani
(74) *Attorney, Agent, or Firm* — ArentFox Schiff LLP

(57)                ABSTRACT

The disclosure is directed to an electrosurgical generator comprising: an electromagnetic signal supply unit for generating electromagnetic, EM, energy to be conveyed along each of a plurality of channels. Each of the plurality of channels is arranged to convey electromagnetic energy at a different frequency. The electrosurgical generator further comprises an output port selectively connectable to each of the plurality of channels. The output port is connectable to an electrosurgical instrument for delivering the electromagnetic energy to biological tissue. The electrosurgical generator further comprises a tissue identification unit comprising a controller configured to: detect a signal indicative of a load impedance at the output port; determine a set of complex impedance values from the detected signals; identify a tissue type from the set of complex impedance values; and generate an output for communicating the identified tissue type to a user.

21 Claims, 5 Drawing Sheets

(52) U.S. Cl.
CPC ............... *A61B 2018/00684* (2013.01); *A61B 2018/00732* (2013.01); *A61B 2018/00785* (2013.01); *A61B 2018/00875* (2013.01); *A61B 2018/00904* (2013.01); *A61B 2018/1823* (2013.01); *A61B 2018/1876* (2013.01)

(58) Field of Classification Search
CPC ...... A61B 2018/128; A61B 2018/1293; A61B 2018/1876; A61B 2018/00845; A61B 2018/00869; A61B 2018/00988; A61B 2018/0075; A61B 2018/00755; A61B 2018/00172; A61B 2018/00577; A61B 2018/00684; A61B 2018/00732; A61B 2018/00785; A61B 2018/00875; A61B 2018/00904; A61B 2018/1823; A61B 2018/00589; A61B 2018/00595; A61B 2018/00607; A61B 2018/0063; A61B 2018/00642; A61B 2018/00648; A61B 2018/00654
USPC ..... 606/32–35, 37–40; 607/98, 99, 101, 113
See application file for complete search history.

(56) References Cited

U.S. PATENT DOCUMENTS

| | | | |
|---|---|---|---|
| 2010/0121318 A1* | 5/2010 | Hancock | A61B 5/0507 342/174 |
| 2010/0145328 A1* | 6/2010 | Hancock | A61B 18/1815 606/33 |
| 2010/0168730 A1 | 7/2010 | Hancock et al. | |
| 2012/0035688 A1 | 2/2012 | Hancock | |
| 2014/0074084 A1 | 3/2014 | Engeberg et al. | |
| 2016/0374752 A1 | 12/2016 | Hancock | |
| 2017/0007308 A1 | 1/2017 | Mun et al. | |
| 2018/0133460 A1 | 5/2018 | Townley et al. | |
| 2019/0201095 A1* | 7/2019 | Hancock | A61B 18/1815 |
| 2020/0261142 A1 | 8/2020 | Panescu et al. | |
| 2020/0289198 A1* | 9/2020 | Hancock | A61B 18/1815 |

OTHER PUBLICATIONS

Search Report Under Section 17, issued by the United Kingdom Intellectual Property Office in corresponding United Kingdom Application No. GB2118160.7, dated Jun. 1, 2022.
International Preliminary Report on Patentability, issued by the International Searching Authority in corresponding International Patent Application No. PCT/EP2022/079248, dated Jun. 7, 2023.

* cited by examiner

ELECTROSURGICAL SYSTEM FOR IDENTIFYING AND TREATING BIOLOGICAL TISSUE

CROSS-REFERENCE TO RELATED APPLICATIONS

This application is a Continuation of U.S. patent application Ser. No. 18/709,737, filed May 13, 2024, now U.S. Pat. No. 12,268,442, which is a National Stage Entry of International Application No. PCT/EP2022/079248, filed Oct. 20, 2022, which claims priority to United Kingdom Patent Application No. 2118160.7, filed Dec. 15, 2021. The disclosures of the priority applications are hereby incorporated in their entirety by reference.

FIELD OF THE INVENTION

The invention relates to an electrosurgical system that is capable of identifying biological tissue at a treatment site. In particular, the invention relates to an electrosurgical generator for selectively supplying electromagnetic energy at a plurality of frequencies along a common feed cable to an electrosurgical instrument that contacts the biological tissue. The electromagnetic energy may be controllable to be suitable for either identification or treatment of biological tissue. Identification of biological tissue may be achieved by determining an impedance of the biological tissue through measurement of electromagnetic energy delivered along and reflected back through the feed cable. The feed cable may be capable of being introduced through an instrument channel of a surgical scoping device (e.g. endoscope or bronchoscope) to treat biological tissue in a minimally invasive manner.

BACKGROUND

Electrosurgical generators are pervasive throughout hospital operating theatres, for use in open and laparoscopic procedures, and are also increasingly present in endoscopy suites. In endoscopic procedures the electrosurgical accessory is typically inserted through a lumen inside an endoscope. Considered against the equivalent access channel for laparoscopic surgery, such a lumen is comparatively narrow in bore and greater in length.

It is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. When an RF voltage is applied to the tissue matrix, enough heat is generated within the cells to vaporise the water content of the tissue. As a result of this increasing desiccation, particularly adjacent to the RF emitting region of the instrument (referred to herein as an RF blade) which has the highest current density of the entire current path through tissue, the tissue adjacent to the cut pole of the RF blade loses direct contact with the blade. The applied voltage then appears almost entirely across this void which ionises as a result, forming a plasma, which has a very high volume resistivity compared to tissue. This differentiation is important as it focusses the applied energy to the plasma that completed the electrical circuit between the cut pole of the RF blade and the tissue. Any volatile material entering the plasma slowly enough is vaporised and the perception is therefore of a tissue dissecting plasma.

GB 2 486 343 discloses a control system for an electrosurgical apparatus which delivers both RF and microwave energy to treat biological tissue. The energy delivery profile of both RF energy and microwave energy delivered to a probe is set based on sampled voltage and current information of RF energy conveyed to the probe and sampled forward and reflected power information for the microwave energy conveyed to and from the probe.

GB 2 522 533 discloses an isolating circuit for an electrosurgical generator arranged to produce radiofrequency (RF) energy and microwave energy for treating biological tissue. The isolating circuit comprises a tunable waveguide isolator at a junction between the microwave channel and signal combiner, and can include a capacitive structure between a ground conductor of the signal combiner and a conductive input section of the waveguide isolator to inhibit coupling of the RF energy and leakage of the microwave energy.

WO 2021/136717 discloses an electrosurgical generator capable of selective delivery of microwave energy at a plurality of different frequencies. The different frequencies may be delivered separately or simultaneously, e.g. to create different effects or biological tissue. To enable efficient delivery of the microwave energy, the electrosurgical generator has a signal combiner capable of effective isolation of a plurality of microwave channels, so that each frequency of energy is directed from its respective channel to an output port with minimal or negligible leakage into channels conveying other frequencies.

The present invention has been devised in light of the above considerations.

SUMMARY OF THE INVENTION

At its most general, the present invention provides an electrosurgical generator that has an integrated tissue identifying function. Through the detection of properties of signal conveyed to and reflected back along energy conveying channels in the generator, information about the dielectric properties of the material to which the energy is delivered can be determined. In particular, when the generator is connected to an electrosurgical instrument configured to delivery the energy into biological tissue, the complex impedance of that tissue can be determined. As different types of tissue can be characterised by their complex impedance, this allows the generator to identify the type of tissue in contact with the instrument. The present invention proposes a tissue identification unit that can detect such properties at a plurality of different frequencies. This may allow the tissue type to be ascertained with greater accuracy. The tissue identifying function may also advantageously be incorporated in to an electrosurgical generator capable of producing electromagnetic energy suitable for tissue treatment, e.g. through ablation, resection, electrocoagulation, electroporation, etc. Indeed, the electrosurgical generator may be capable of performing tissue identification and treatment using the same instrument, which is advantageous for the efficacy of surgical procedures, especially those where the instrument is conveyed to the treatment site through a surgical scoping device, such as a endoscope.

According to one aspect of the invention, there is provided an electrosurgical generator comprising: an electromagnetic signal supply unit for generating electromagnetic, EM, energy to be conveyed along each of a plurality of channels, wherein each of the plurality of channels is arranged to convey electromagnetic energy at a different frequency; an output port selectively connectable to each of the plurality of channels, wherein the output port is configured to be connectable to an electrosurgical instrument for delivering the electromagnetic energy to biological tissue; a tissue identification unit comprising a controller configured to: detect, from each of the plurality of channels, a signal indicative of a load impedance at the output port; determine a set of complex impedance values from the detected signals, wherein the set of complex impedance values comprise a complex impedance value for the load at each of a plurality of different frequencies; identify a tissue type from the set of complex impedance values; and generate an output for communicating the identified tissue type to a user. In the use, the electrosurgical generator may be connected to the electrosurgical instrument via a suitable transmission line (e.g. coaxial cable) connected between the output port and the electrosurgical instrument. When the electrosurgical instrument is moved to a treatment site, the electrosurgical generator may be operated in an tissue identification mode to transmit signals to the instrument down each of the plurality of channels. The electrosurgical generator may include a switch operable to select one of the plurality of channels to deliver energy to the instrument. The set of complex impedance values is assembled by switching through the channels and detecting the signal indicative of a load impedance at the output port for each channel. The load impedance in this scenario is actually the load at the distal end of the instrument, e.g. biological tissue in contact with the instrument. The controller uses the set of complex impedance values to determine a tissue type, e.g. with reference to a look up table or library of complex impedances for known tissue types. The output may be a message or other indicator on a display provided on a user interface (e.g. computer terminal, laptop, tablet or the like) that identifies the tissue type.

The invention may be used to distinguish healthy tissue from cancerous tissue, and may for example assist in positioning the tip of the instrument in a location in the treatment site or in ascertaining the volume of tissue requiring treatment. In particular, the tissue identification unit may be configured to detect a boundary between healthy and cancerous tissue. This information is very useful for planning a treatment procedure. For example, if treatment involves ablation of a large tumour (e.g. 6 cm), the ability to distinguish between homogeneous tumour, ablated tissue/tumour and a boundary of healthy tissue enable the location of the probe to be optimised to ensure that the complete tumour is ablated using a minimal number of repositioning of the probe. For example, ablation of large tumours may be carried out in multiple steps, with the probe located in two or more positions that are spaced away from the geometric centre or centre of mass of the tumour. Knowledge of the location of the tumour boundary can assist in determining the optimum number and locations of these positions, which may be particularly useful for planning treatment that is assisted by robotic control.

In particular, the tissue identification function of the invention may be able to distinguish between one or more of: tumour tissue; airway (e.g. either an air-filled volume or a mucus-filled volume); healthy tissue (include for example the ability to distinguish between healthy tissue types, such as muscle, lung, fat, liver, brain, etc.); and ablated material (for example ablated healthy tissue or ablated tumour). Using this information, the generator may be able to generator an output that identifies in real time the type of tissue in contact with the instrument.

Furthermore, the tissue identification unit may be configured to detect one or more boundaries between different tissue types. In some examples, the electromagnetic signal supply unit may be automatically controllable based on the detection of a boundary, for example to switch off an ablating signal immediately upon detection of a boundary between cancerous and healthy tissue. Additionally or alternatively, the detection of different boundaries may be undertaken as a preliminary (pre-treatment) step to determine a pathway for a robot-assisted movement of the instrument during a subsequent treatment step. The tissue identification unit may be configured to detect any one or more of a boundary between non-ablated healthy tissue and ablated tissue; a boundary between non-ablated tumour and ablated tissue; and a boundary between healthy (non-cancerous) tissue and (non-ablated) tumour tissue.

The generator may be configured to deliver energy for tissue identification at a lower power than that used for tissue treatment. The power level used for tissue identification may be selected depending on receiver sensitivity. The power level for tissue identification may be greater than 100 µW and less than 1 W, preferably greater than or equal to 0.5 mW and less than or equal to 100 mW, more preferably greater than or equal to 1 mW and less than or equal to 20 mW.

The electromagnetic signal supply unit may be configured to generating microwave EM energy at a plurality of microwave frequencies, and wherein the plurality of channels comprises at least two channels configured to convey microwave EM energy. For example, the plurality of microwave frequencies may include any of 433 MHz, 915 MHz, 2.45 GHz, 3.3 GHz, 5.8 GHz, 10 GHz, 14.5 GHz, 24 GHz and 60 GHz. The higher frequencies in this list may be particularly useful for obtaining localised impedance measurements.

The tissue identification unit may comprise, on each of the plurality of microwave channels: a forward detector configured to detect a forward signal indicative of microwave EM energy travelling towards the output port; and a reverse detector configured to detect a reflected signal indicative of microwave EM energy travelling away from the output port. The forward detector may be a coupler. The reverse detector may be implemented using a circulator configured to separate reflected energy from the forward signal. The tissue identification unit may be arranged to use the forward signal and the reflected signal detected on each of the plurality of microwave channels as the signal indicative of a load impedance at the output port for that microwave channel. In other words, the load impedance can be obtained from a reflection coefficient that can be calculated using the forward and reflected signals in a conventional manner. To facilitated determination of the load impedance, each microwave channel includes a heterodyne receiver configured to: receive the forward signal and the reflected signal as inputs; receive a reference signal have an frequency offset from the frequency of the forward signal and the reflected signal; and generate a forward detection signal and a reflected detection signal that have an intermediate frequency obtained by mixing down the forward signal and the reflected signal with the reference signal. The mixed down signal may be more suitable for processing at the controller. For example, the controller may be arranged to receive and digitise the forward detection signal and the reflected detection signal, and calculate a complex impedance using the digitised forward detection signal and reflected detection signal. The set of complex impedances may comprise a complex impedance calculated from the digitised forward detection signal and reflected detection signal for each of the plurality of microwave channels. The calculation may be performed by a field-programmable gate array, for example.

In a particularly advantageous example, the reference signal for each of the plurality of microwave channels is selected to cause the forward detection signal and reflected detection signal for each of the plurality of microwave channels to have a common intermediate frequency. In other words, all of the forward detection signals and reflected detection signals received at the controller may have the same frequency. This may mean that the same calculation logic (e.g. in the FPGA) may be used for each microwave channel. The common intermediate frequency may be equal to or less than 100 MHz, e.g. 50 MHz.

The electromagnetic signal supply unit may be also be configured to generate radiofrequency, RF, EM energy and use the RF energy for tissue identification. The plurality of channels may thus comprise an RF channel configured to convey the RF EM energy. The RF EM energy may have a frequency equal to or less than 400 MHz.

The RF channel may be coupled to the output port through an output transformer in order to any current paths directly from the electromagnetic signal supply unit. The tissue identification unit may be configured to detect a characteristic impedance on the primary coil side of the output transformer in order to ascertain information about a load impedance (biological tissue) in the circuit on the secondary side of the output transformer. For example, the tissue identification unit may be configured to determine an input impedance (on the primary coil side of the output transformer) by detecting voltage and current conditions in the primary circuit.

In one example, the tissue identification unit comprises, on the RF channel: a current transformer configured to determine a signal indicative of current in the primary coil of the output transformer; a voltage divider configured to determine a signal indicative of voltage across the primary coil of the output transformer; and a comparator configured to determine a signal indicative of a phase difference between the voltage across and current in the output transformer, wherein the tissue identification unit is arranged to use the signals indicative of voltage, current and phase difference as the signal indicative of a load impedance at the output port for the RF channel. Similarly to the microwave channels discussed above, the controller may be arranged to receive and digitise the signals indicative of voltage, current and phase difference, and calculate a complex impedance using these digitised signals. The controller may include a field-programmable gate array configured to calculate the complex impedance.

The set of complex impedances may thus comprise a complex impedance calculated from the digitised signals obtained from the RF channel, e.g. in addition to complex impedance signal calculated from one or more microwave channels.

The electrosurgical generator may comprise any combination of one or more RF channels and one or more microwave channels.

The controller may be configured to apply a calibration adjustment when determining the set of complex impedance values from the detected signals. The calibration adjustment may be predetermined by exposing the output port to a plurality (e.g. three or more) calibration standards, e.g. loads having known complex impedances that are different from one another. For example, the calibration standard may include deionised water, anhydrous ethanol and a 50:50 mixture of deionised water and anhydrous ethanol.

In some example, especially where there is a long distance between the electrosurgical generator and the instrument, it is possible that intervening components, e.g. a flexible transmission line for conveying the energy, may introduce a phase shift into the conveyed energy. If the transmission line shifted position, e.g. due to movement of the instrument to a new location, it is possible that the phase shift will change. It may therefore be desirable to measure the phase shift so that its effects do no adversely affect the tissue identification process. The electrosurgical generator may thus be used with a flexible transmission line connected to the output port for conveying the electromagnetic energy to the electrosurgical instrument. The flexible transmission line may include a selectively reflective element mounted at a distal end thereof. The plurality of channels may include a first channel arranged to convey electromagnetic energy at a first frequency, and a second channel arranged to convey electromagnetic energy at a second frequency that is different from the first frequency, wherein the selectively reflective element has an electrical length that is an odd multiple quarter wavelength at the second frequency, and a multiple half wavelength at the first frequency. This means that the selectively reflective element reflects energy at the second frequency before it enters the instrument, but is transparent to the energy at the first frequency, which therefore passes into the instrument. The controller may be configured to detect a phase offset from energy conveyed on the second channel by determining a phase change between forward and reflected signals on the second channel. The controller may apply the phase offset when determining a complex impedance value from the detected signal on the first channel. In this manner the electrosurgical generator can compensate for phase variations along the signal pathway to the instrument.

The electromagnetic signal supply unit may be configured to generate microwave EM energy for tissue ablation, and convey the microwave EM energy for tissue ablation to the output port along a dedicated channel that is independent of the tissue identification unit.

The controller may include a memory storing a look up table or digital library that contains known complex impedances for a plurality of tissues types at different frequencies. The controller may be configured to identify a tissue type by comparing the set of complex impedance values to the known complex impedances. For example, the controller may include an algorithm arranged to determine a "best fit" between the set of complex impedances and known complex impedances for a given tissue type. The algorithm may be configured to generate a confidence score that is indicative of how closely the set of complex impedance values match the known complex impedances. The confidence score may be communicated with the tissue type.

Alternatively or additionally, the controller may be configured to generate an output for communicating the identified tissue type upon determine a match between more than one complex impedance value in the set of complex impedance values and known complex impedances at corresponding frequencies.

The electrosurgical generator discussed above may be connected to a probe, e.g. via a coaxial transmission line extending from the output port. The probe may comprise an electrosurgical instrument suitable for insertion through an instrument channel in a surgical scoping device. The electrosurgical instrument may have a distal end assembly configured to output any of the RF, microwave and electroporation energy discussed herein. In one example, the distal end assembly may include a coaxial structure in which an inner conductor protrudes beyond a distal end of an outer conductor and exposed at the distal end of the probe. With this configuration, the distal end assembly formed a bipolar energy delivery structure for delivering RF energy and a microwave antenna for radiating microwave energy.

In this specification "microwave" may be used broadly to indicate a frequency range of 400 MHz to 100 GHz, but preferably the range 400 MHz to 60 GHz. Specific frequencies that have been considered are: 433 MHz, 915 MHz, 2.45 GHz, 3.3 GHz, 5.8 GHz, 10 GHz, 14.5 GHz, 24 GHz and 60 GHz. The device may delivery energy at more than one of these microwave frequencies. The term "radiofrequency" or "RF" may be used to indicate a frequency between 300 kHz and 400 MHz.

Herein, the term "inner" means radially closer to the centre (e.g. axis) of the instrument channel. The term "outer" means radially further from the centre (axis) of the instrument channel.

The term "conductive" is used herein to mean electrically conductive, unless the context dictates otherwise.

Herein, the terms "proximal" and "distal" refer to the ends of the energy conveying structure further from and closer to the treatment site respectively. Thus, in use the proximal end is closer to a generator for providing the microwave energy, whereas the distal end is closer to the treatment site, i.e. the patient.

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

Background

Figure 1:
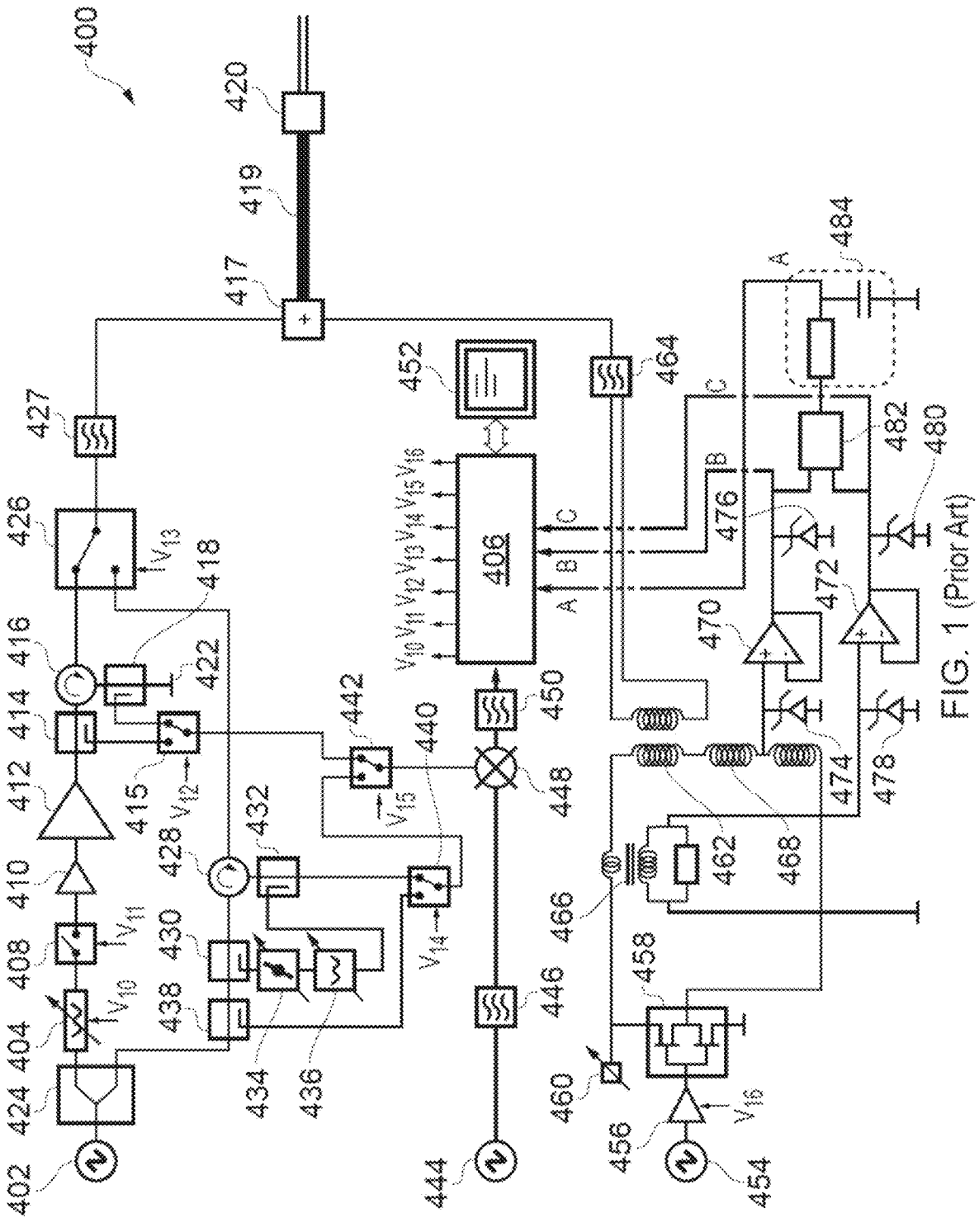
FIG. 1 is a schematic diagram of a known type of electrosurgical generator.

FIG. 1 shows a schematic diagram of an electrosurgical apparatus 400 such as that disclosed in GB 2 486 343 that is useful for understanding the invention. The apparatus comprises a RF channel and a microwave channel. The RF channel contains components for generating and controlling an RF frequency electromagnetic signal at a power level suitable for treating (e.g. cutting or desiccating) biological tissue. The microwave channel contains components for generating and controlling a microwave frequency electromagnetic signal at a power level suitable for treating (e.g. coagulating or ablating) biological tissue.

The microwave channel has a microwave frequency source 402 followed by a power splitter 424 (e.g. a 3 dB power splitter), which divides the signal from the source 402 into two branches. One branch from the power splitter 424 forms a microwave channel, which has a power control module comprising a variable attenuator 404 controlled by controller 406 via control signal $V_{10}$ and a signal modulator 408 controlled by controller 406 via control signal $V_{11}$, and an amplifier module comprising drive amplifier 410 and power amplifier 412 for generating forward microwave EM radiation for delivery from a probe 420 at a power level suitable for treatment. After the amplifier module, the microwave channel continues with a microwave signal coupling module (which forms part of a microwave signal detector) comprising a circulator 416 connected to deliver microwave EM energy from the source to the probe along a path between its first and second ports, a forward coupler 414 at the first port of the circulator 416, and a reflected coupler 418 at the third port of the circulator 416. After passing through the reflected coupler, the microwave EM energy from the third port is absorbed in a power dump load 422. The microwave signal coupling module also includes a switch 415 operated by the controller 406 via control signal $V_{12}$ for connecting either the forward coupled signal or the reflected coupled signal to a heterodyne receiver for detection.

The other branch from the power splitter 424 forms a measurement channel. The measurement channel bypasses the amplifying line-up on the microwave channel, and hence is arranged to deliver a low power signal from the probe. A primary channel selection switch 426 controlled by the controller 406 via control signal $V_{13}$ is operable to select a signal from either the microwave channel or the measurement channel to deliver to the probe. A high band pass filter 427 is connected between the primary channel selection switch 426 and the probe 420 to protect the microwave signal generator from low frequency RF signals.

The measurement channel includes components arranged to detect the phase and magnitude of power reflected from the probe, which may yield information about the material e.g. biological tissue present at the distal end of the probe. The measurement channel comprises a circulator 428 connected to deliver microwave EM energy from the source 402 to the probe along a path between its first and second ports. A reflected signal returned from the probe is directed into the third port of the circulator 428. The circulator 428 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit may be used that injects a portion of the forward signal (from forward coupler 430) back into the signal coming out of the third port (via injection coupler 432). The carrier cancellation circuit include a phase adjustor 434 to ensure that the injected portion is 180° out of phase with any signal that breaks through into the third port from the first port in order to cancel it out. The carrier cancellation circuit also include a signal attenuator 436 to ensure that the magnitude of the injected portion is the same as any breakthrough signal.

To compensate for any drift in the forward signal, a forward coupler 438 is provided on the measurement channel. The coupled output of the forward coupler 438 and the reflected signal from the third port of the circulator 428 are connected to respective input terminal of a switch 440, which is operated by the controller 406 via control signal $V_{14}$ to connect either the coupled forward signal or the reflected signal to a heterodyne receiver for detection.

The output of the switch 440 (i.e. the output from the measurement channel) and the output of the switch 415 (i.e. the output from the microwave channel) are connect to a respective input terminal of a secondary channel selection switch 442, which is operable by the controller 406 via control signal $V_{15}$ in conjunction with the primary channel selection switch to ensure that the output of the measurement channel is connected to the heterodyne receiver when the measurement channel is supplying energy to the probe and that the output of the microwave channel is connected to the heterodyne receiver when the microwave channel is supplying energy to the probe.

The heterodyne receiver is used to extract the phase and magnitude information from the signal output by the secondary channel selection switch 442. A single heterodyne receiver is shown in this system, but a double heterodyne receiver (containing two local oscillators and mixers) to mix the source frequency down twice before the signal enters the controller may be used if necessary. The heterodyne receiver comprises a local oscillator 444 and a mixer 448 for mixing down the signal output by the secondary channel selection switch 442. The frequency of the local oscillator signal is selected so that the output from the mixer 448 is at an intermediate frequency suitable to be received in the controller 406. Band pass filters 446, 450 are provided to protect the local oscillator 444 and the controller 406 from the high frequency microwave signals.

The controller 406 receives the output of the heterodyne receiver and determines (e.g. extracts) from it information indicative of phase and magnitude of the forward and/or reflected signals on the microwave or measurement channel. This information can be used to control the delivery of high power microwave EM radiation on the microwave channel or high power RF EM radiation on the RF channel. A user may interact with the controller 406 via a user interface 452.

The RF channel shown in FIG. 1 comprises an RF frequency source 454 connected to a gate driver 456 that is controlled by the controller 406 via control signal $V_{16}$. The gate driver 456 supplies an operation signal for an RF amplifier 458, which is a half-bridge arrangement. The drain voltage of the half-bridge arrangement is controllable via a variable DC supply 460. An output transformer 462 transfers the generated RF signal on to a line for delivery to the probe 420. A low pass, band pass, band stop or notch filter 464 is connected on that line to protect the RF signal generator from high frequency microwave signals.

A current transformer 466 is connected on the RF channel to measure the current delivered to the tissue load. A potential divider 468 (which may be tapped off the output transformer) is used to measure the voltage. The output signals from the potential divider 468 and current transformer 466 (i.e. voltage outputs indicative of voltage and current) are connected directly to the controller 406 after conditioning by respective buffer amplifiers 470, 472 and voltage clamping Zener diodes 474, 476, 478, 480 (shown as signals B and C in FIG. 1).

To derive phase information, the voltage and current signals (B and C) are also connected to a phase comparator 482 (e.g. an EXOR gate) whose output voltage is integrated by RC circuit 484 to produce a voltage output (shown as A in FIG. 1) that is proportional to the phase difference between the voltage and current waveforms. This voltage output (signal A) is connected directly to the controller 406.

The microwave/measurement channel and RF channel are connected to a signal combiner 417, which conveys both types of signal separately or simultaneously along cable assembly 419 to the probe 420, from which it is delivered (e.g. radiated) into the biological tissue of a patient.

A waveguide isolator (not shown) may be provided at the junction between the microwave channel and signal combiner 417. The waveguide isolator may be configured to perform three functions: (i) permit the passage of very high microwave power (e.g. greater than 10 W); (ii) block the passage of RF power; and (iii) provide a high withstanding voltage (e.g. greater than 10 kV). A capacitive structure (also known as a DC break) may also be provided at (e.g. within) or adjacent the waveguide isolator. The purpose of the capacitive structure is to reduce capacitive coupling across the isolation barrier.

Figure 2:
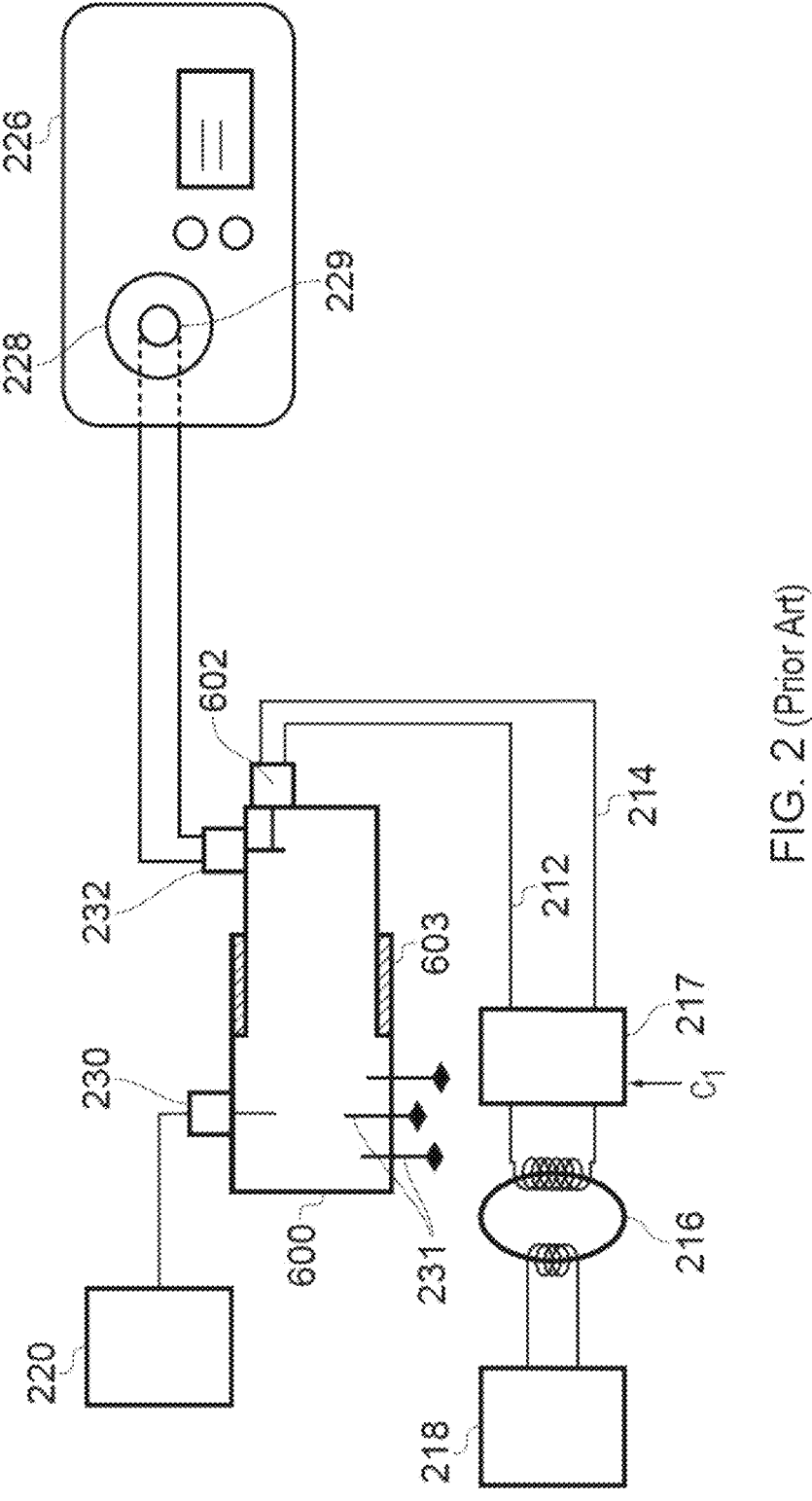
FIG. 2 is a schematic diagram of an isolating circuit that can be used in an electrosurgical generator of FIG. 1.

FIG. 2 is a schematic diagram of an isolating circuit as disclosed in GB 2 522 533, which is also useful for understanding the invention. The isolating circuit forms part of a feed structure for conveying RF EM radiation from an RF signal generator 218 and microwave radiation from a microwave signal generator 220 to a probe. The probe (not shown) is connectable to an output port 228 provided in a housing 226. An insulating sleeve 229 is provided at the output port 228 of the housing to prevent a current path for connecting the grounded casing of the housing with the floating components connected to the output port 228.

The feed structure comprises an RF channel having a RF signal pathway 212, 214 for conveying the RF EM radiation and a microwave channel having a microwave signal pathway 210 for conveying the microwave EM radiation. The signal pathways for the RF EM radiation and microwave radiation are physically separate from each other. The RF signal generator is connected to the RF signal pathway 212, 214 via a voltage transformer 216. The secondary coil of the transformer 216 (i.e. on the probe side of the arrangement) is floating, so there is not direct current path between the patient and the RF signal generator 218. This means that both the signal conductor 212 and ground conductor 214 of the RF signal pathway 212, 214 are floating.

The isolating circuit comprises a waveguide isolator 600 whose insulating gap is configured to provide the necessary level of DC isolation whilst also having a capacitive reactance that is low enough at the frequency of the microwave energy to prevent leakage of the microwave energy at the gap. The gap may be 0.6 mm or more, e.g. 0.75 mm. RF energy is not able to couple between the two ends of the isolator because the diameter of the tube creates a very large inductance in series with each of the probes at the RF frequency.

The isolating circuit has a combining circuit integrated with the waveguide isolator 600. A signal conductor 212 and ground conductor 214 carrying the RF signal are connected to a coaxial RF connector 602 (RF feed), which introduces the RF signal into the waveguide isolator 600, from where it is conveyed out from an output port 232 towards the probe.

The isolating gap 603 is arranged to prevent the RF signal from coupling back into the input port 230. Microwave energy is prevented from coupling into the RF connector 602 by careful placement of the inner conductive rod within the waveguide isolator.

A tuning unit is incorporated into the waveguide isolator 600 in order to reduce the return loss of the line-up of components. The tuning unit comprises three stubs 231 that can be adjustably inserted, e.g. screwed, into the body of the cavity.

In addition, the RF channel has an adjustable reactance 217 that is operable under the control of control signal $C_1$ to accommodate (e.g. compensate for) changes in capacitance arising from different lengths of cable used with the generator. The adjustable reactance 217 may comprise one or more of switched or electronically tunable capacitors or inductors connected in shunt or series with the RF channel.

Figure 3:
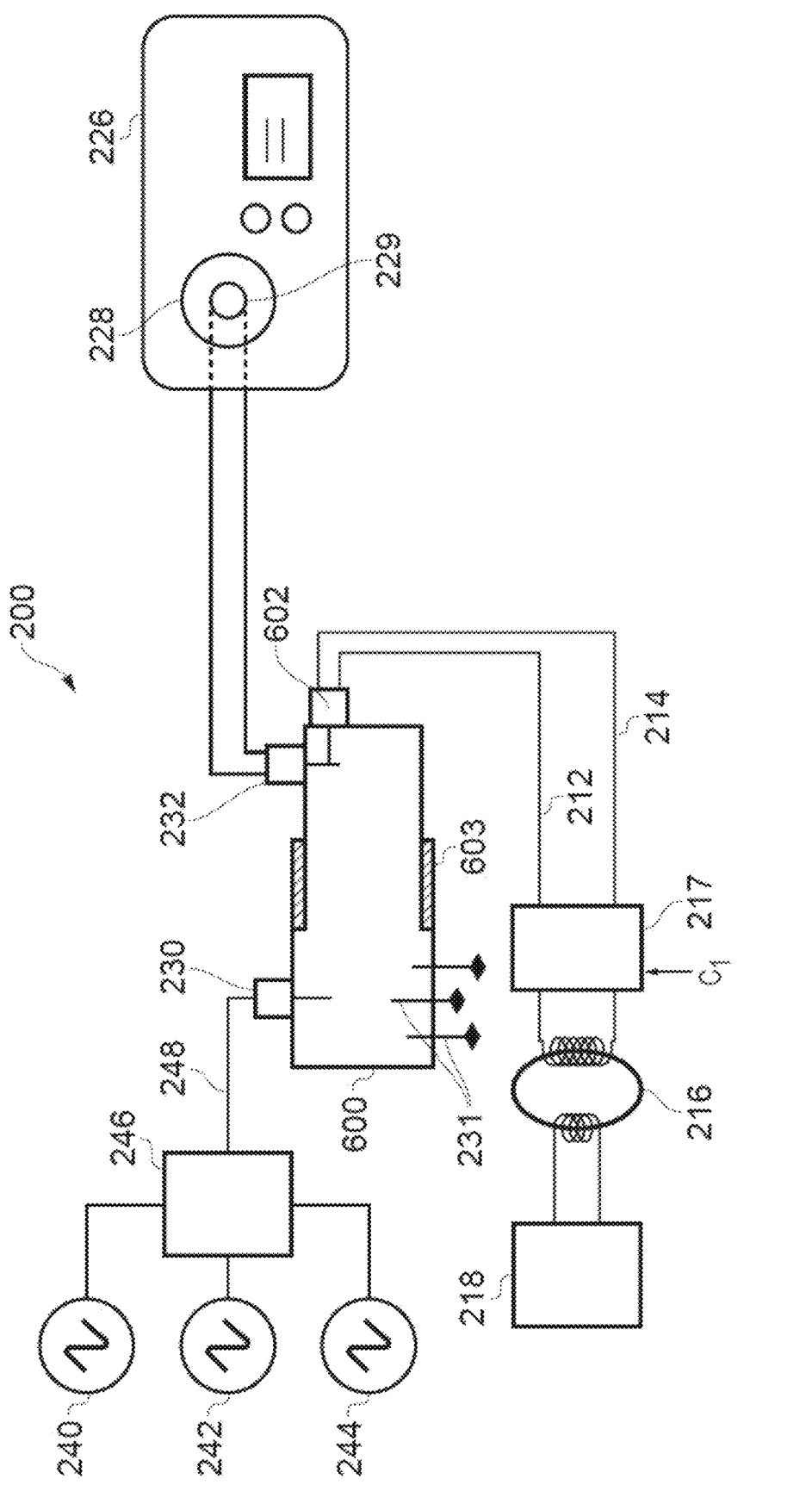
FIG. 3 is a schematic diagram of a known type of electrosurgical generator capable of delivering microwave energy at multiple frequencies.

FIG. 3 is a schematic diagram of an electrosurgical generator 200 that is configured to supply a plurality of microwave frequencies. The overall architecture of the electrosurgical generator 200 may similar to that discussed above with respect to FIG. 1, and it may include an isolating circuit as discussed with respect to FIG. 2 to combined RF and microwave energy.

The electrosurgical generator 200 differs from FIGS. 1 and 2 in that it comprises a plurality of microwave channels 240, 242, 244, each configured to generate microwave energy having a particular frequency different from the other microwave channels. The plurality of microwave channels 240, 242, 244 may each comprise a separate (independent) microwave source. Alternatively, the signals on each microwave channel may be derived from a single source, with suitable frequency multiplication or division.

Each of the plurality of microwave channels may be operable (e.g. activatable) independently. Microwave signals having differing frequencies can be thus be supplied separately or simultaneously from the plurality of microwave channels.

The electrosurgical generator 200 further comprises a microwave signal combiner 246 having a set of input ports configured to receive a microwave signal from each of the plurality of microwave channels 240, 242, 244. The microwave signal combiner 246 also has an output port from which the signals from the microwave channels 240, 242, 244 are conveyed along a common transmission line 248 to the input port 230 of the waveguide isolator 600.

The plurality of microwave channels 240, 242, 244 may be arranged to generate a microwave signal at any suitable frequency. However, it may be preferred for the generated frequencies to belong to one of the following ISM bands:
- 433.05 MHz to 434.79 MHz (1.74 MHz bandwidth with a centre frequency 433.92 MHz)
- 902 MHz to 928 MHz (26 MHz bandwidth with a centre frequency at 915 MHz)
- 2.4 GHz to 2.5 GHz (100 MHz bandwidth with centre frequency of 2.45 GHz)
- 5.725 GHz to 5.875 GHz (150 MHz bandwidth with a centre frequency of 5.8 GHz)
- 24.0 GHz to 24.25 GHz (250 MHz bandwidth with a centre frequency 24.125 MHz)
- 61.0 GHz to 61.5 GHz (500 MHz bandwidth with a centre frequency 61.25 GHz).

The microwave channels may generate signals from any combination of two or more of the above bands.

Tissue Treatment and Identification at Multiple Frequencies

Figure 4:
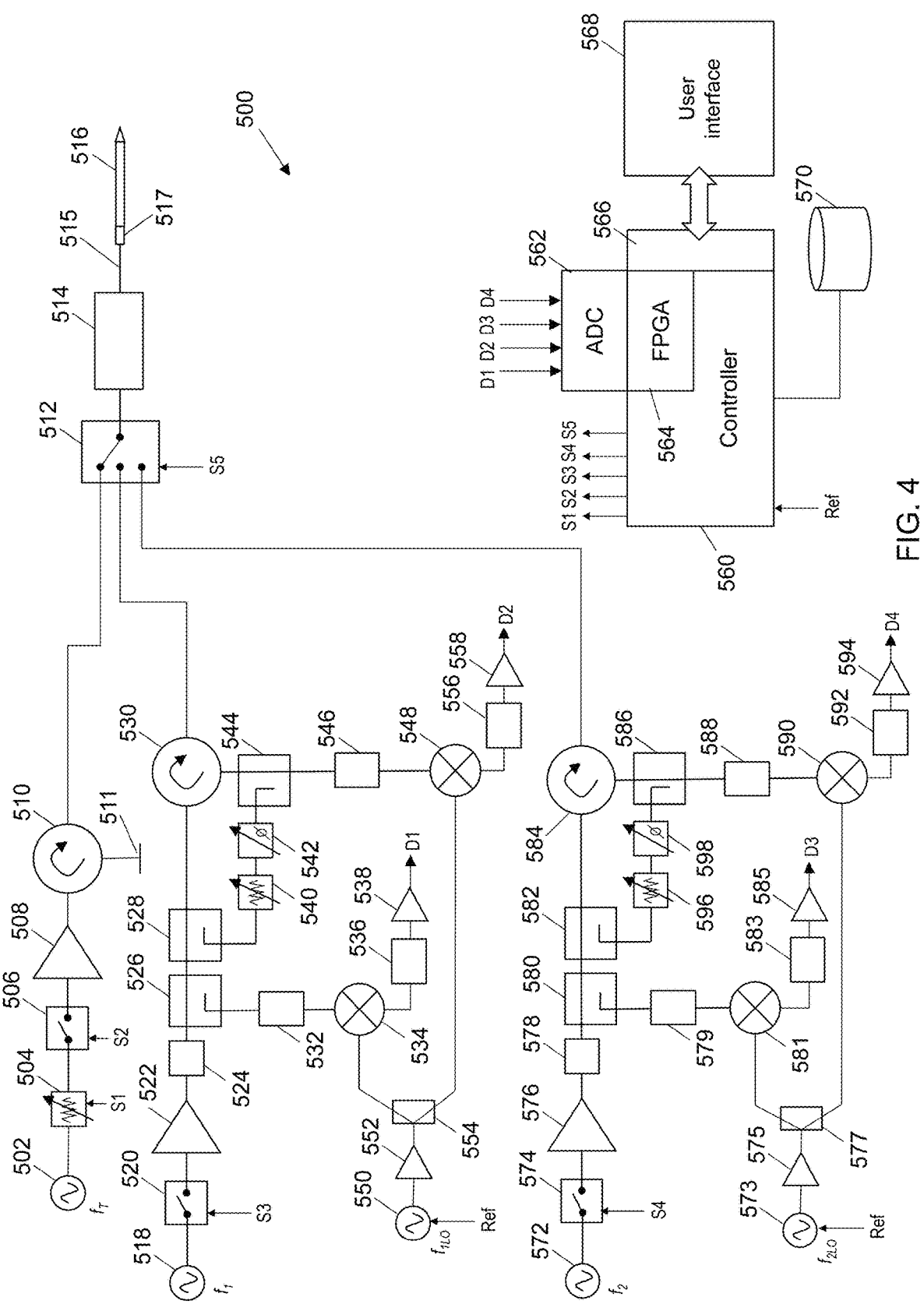
FIG. 4 is a schematic diagram of an electrosurgical generator having a plurality of microwave frequency channels and a tissue identification function that is an embodiment of the invention.

FIG. 4 is a schematic diagram of an electrosurgical generator 500 that is an embodiment of the invention. In this example, the electrosurgical generator 500 has three microwave channels which operate at different frequencies. However, it is to be understood that the invention is not limited to this configuration. For example, the electrosurgical generator 500 may include additional microwave channels and/or may include an RF channel such as that described below with reference to FIG. 5.

Figure 5:
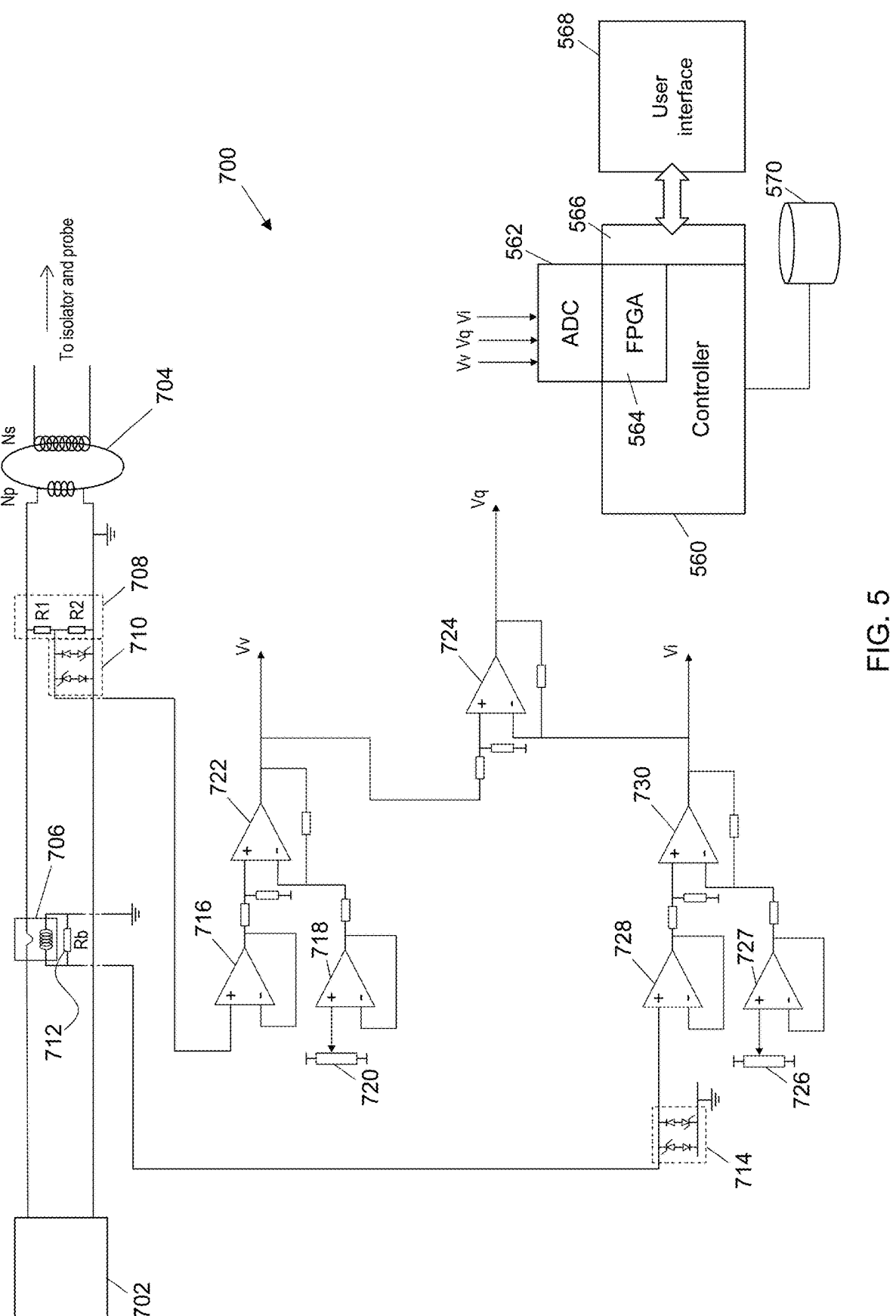
FIG. 5 is a schematic diagram of a radiofrequency (RF) channel with a tissue identification function that is suitable for use in an electrosurgical generator that is an embodiment of the invention.

In the electrosurgical generator 500 shown in FIG. 5, the three microwave channels comprise a first microwave channel that starts with a first microwave source 502, which generates a microwave signal having a frequency $f_T$, a second microwave channel that starts with a second microwave source 518, which generates a microwave signal having a frequency $f_1$, and a third microwave channel that starts with a third microwave source 572, which generates a microwave signal having a frequency $f_2$. Each of the first, second and third microwave source 502, 518, 572 may be a separate (independent) microwave source. Alternatively, the signals on each microwave channel may be derived from a single source, with suitable frequency multiplication or division.

The first microwave channel is configured as a treatment-only channel, in that it is configured to generate a microwave signal having a power level suitable for tissue ablation or coagulation. The first microwave channel has a power control module comprising a variable attenuator 504 controlled by controller 560 via control signal $S_1$ and a signal modulator 506 controlled by controller 560 via control signal $S_2$, and an amplifier module 508 (e.g. comprising drive amplifier and power amplifier) for generating forward microwave EM radiation for delivery from an electrosurgical instrument 516 at a power level suitable for treatment. After the amplifier module 508, the microwave channel continues with a circulator 510 connected to deliver microwave EM energy from the source to the probe along a path between its first and second ports. Any backward travelling energy received at the second port of the circulator 510 is transferred to the third port to be absorbed in a power dump load 511.

The first microwave channel ends at a switch 512, which is operated by the controller 560 via control signal $S_5$ to select a signal from one of the microwave channels to be delivered to the probe 516 via an isolating circuit 514, which may be configured as shown in FIG. 3, and a cable 515. The switch 512 may be a PIN switch, or a coaxial switch or a waveguide switch.

The second and third microwave channels are both configured as channels that are capable of both treatment and identification.

The second microwave channel has a power control module 520 (e.g. comprising a variable attenuator and signal modulator similar to the first microwave channel) controlled by controller 560 via control signal $S_3$, and an amplifier module 522 (e.g. comprising drive amplifier and power amplifier) for generating forward microwave EM radiation for delivery from an electrosurgical instrument 516. After the amplifier module 522, the second microwave channel continues with an isolator 524 configured to protect the amplifier module 522 from backpropagating energy. After the isolator, the second microwave channel continues with a forward coupler 526, which generates a signal representing the forward microwave EM radiation. This signal is attenuated by attenuator 532 before being input to a heterodyne receiver for detection.

The attenuators for the forward and reflected signals are configured to have differing attenuation coefficients. For example, the forward signal may pass through a −6 dB attenuator, while the reflected signal passed through a −12 dB attenuator. The reflected signal is subject to lower attenuation because it will be attenuated by twice the insertion loss of the transmission line that connects the generator to the instrument. For example, if the insertion loss of the transmission line is 6 dB, and the loss of the antenna in the instrument is 0.5 dB, even if the end of the instrument is connected to a perfect short/open circuit (0 dB return loss) the reflected signal will be 13 dB lower at the receiver than the corresponding forward signal. If the forward signal has a power of 10 mW (+10 dBm), then the signal at the receiver would be +10 dBm−13 dB=−3 dBm. On the other hand, if the return loss or match was such that 99% of the power was delivered into the tissue sample then the return loss at the sample load would be −20 dB, then the power level at the receiver would be: +10 dBm−13 dB−20 dB=−23 dBm.

Meanwhile, the second microwave continues with a circulator 530 connected to deliver the forward microwave EM energy to the instrument 516 along a path between its first and second ports. A reflected signal returned from the instrument 516 is directed into the third port of the circulator 530. The circulator 530 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit may be used that injects a portion of the forward signal (from a forward coupler 528) back into the signal coming out of the third port (via injection coupler 544). The carrier cancellation circuit include a phase adjustor 542 to ensure that the injected portion is 180° out of phase with any signal that breaks through into the third port from the first port in order to cancel it out. The carrier cancellation circuit also include a signal attenuator 540 to ensure that the magnitude of the injected portion is the same as any breakthrough signal.

The reflected signal from the third port of the circulator 530 is attenuated by attenuator 546 before being input to the heterodyne receiver for detection.

The heterodyne receiver is used to extract phase and magnitude information from the forward and reflected signal received from the forward coupler 526 and third port of the circulator 530. The heterodyne receiver comprises a first local oscillator 550 that outputs a signal having a frequency $f_{1LO}$ that is slightly offset from the frequency fb of the second microwave source 518. The signal output by the first local oscillator 550 is derived from a common stable reference signal, which is also communicated to the controller 560. The reference signal may be used to reduce noise when a differential measurement is made, for example to remove common mode noise.

The output signal from the first local oscillator 550 is input to amplifier 552 and then split into two separate signals by power splitter 554. These separate signals are input to respective mixers 534, 548 for mixing down the forward signal and the reflected signal from the forward coupler 526 and third port of the circulator 530. The frequency of the local oscillator signal is selected so that the output from the mixers 534, 548 is at an intermediate frequency suitable to be received by an analog to digital converter (ADC) 562 at the controller 560. The mixed down signal from each mixer 534, 548 is input to an integrated filter amplifier (e.g. comprising a band pass filter 536, 556 and amplifier 538, 558) which function to protect the first local oscillator 550 and the controller 560 from any high frequency microwave signals.

The ADC 562 is configured to receive outputs D1, D2 from the heterodyne receiver that correspond to a forward signal delivered to the instrument 516 and a reflected signal received back from the instrument 516. The instrument 516 itself is configured to contact biological tissue for the purpose of transferring the microwave EM energy into the tissue. When the instrument 516 is in contact with tissue, the forward and reflected signals can be used to determine a complex impedance of the load (biological tissue) at the distal end of the instrument.

In this example, the controller 560 includes a field-programmable gate array (FPGA) 564 that is configured to translate the input from the heterodyne receiver (for from each heterodyne receiver in cases where more than one microwave channel is configured to provide tissue identification signals) into a tissue identification output signal that is communicated to a user interface 568 through a suitable connection interface 566 (e.g. Serial Peripheral Interface). The tissue identification output signal may be representative of a known tissue type, or may indicate that the instrument is in air, or may indicate that the load in contact with the instrument is unknown.

To generate the tissue identification output signal, the ADC 562 and FPGA 564 may be configured as a vector network analyser to extract magnitude and phase information for the forward and reflected signals using the received outputs D1, D2 from the heterodyne receiver in order to calculate a complex impedance for the load at the instrument 516, then apply a calibration adjustment to the calculated complex impedance, and finally compare the calibrated complex impedance to a look up table (e.g. stored in memory 570). The look up table may include information about the dielectric properties of a plurality of known tissue types, e.g. obtained from a suitable biobank such as that assembled by the Foundation for Research on Information Technologies in Society (IT'IS).

A particular advantage of the present invention may be the provision of a look up table that provides the dielectric properties of a plurality of known tissue types at a plurality of different frequencies, e.g. corresponding to the frequencies of the microwave channels that are configured to provide tissue identification signals. In this example, the controller may be configured to compare each of a plurality of complex impedances for the same load measured at different frequencies with respective look up tables of complex impedance values for the corresponding frequency. If there is a match between the calibrated complex impedance and a value in the table, a candidate for the tissue type at the instrument can be identified. By running this identification over multiple frequencies, increased confidence in the accuracy of detection is obtained, especially when the same tissue type is identified at multiple frequencies.

The user interface 568 may be configured to display the tissue types obtained by finding a match between the calibrated complex impedance and the entries in the look up table. In some examples, the user interface 568 may also provide a confidence score for the displayed tissue type, e.g. determined based on the number of frequencies at which that tissue type was identified.

The calibration adjustment may be determined in advance by obtaining outputs D1, D2 when the instrument is in contact with a plurality of test loads having a known complex impedance. In one example, three test loads are used to provide a set of complex impedances at different locations on the Smith chart. The three test loads may be deionised water (effectively an open circuit condition), anhydrous ethanol, and a 50:50 mixture of deionised water and anhydrous ethanol. Each microwave channel may be calibrated in the same way.

The third microwave channel is configured in a similar manner to the second microwave channel. The third microwave channel has a power control module 574 (e.g. comprising a variable attenuator and signal modulator similar to the first microwave channel) controlled by controller 560 via control signal $S_4$, and an amplifier module 576 (e.g. comprising drive amplifier and power amplifier) for generating forward microwave EM radiation for delivery from an electrosurgical instrument 516. After the amplifier module 576, the third microwave channel continues with an isolator 578 configured to protect the amplifier module 576 from backpropagating energy. After the isolator, the third microwave channel continues with a forward coupler 580, which generates a signal representing the forward microwave EM radiation. This signal is attenuated by attenuator 604 before being input to a heterodyne receiver for detection.

Meanwhile, the third microwave continues with a circulator 584 connected to deliver the forward microwave EM energy to the instrument 516 along a path between its first and second ports. A reflected signal returned from the instrument 516 is directed into the third port of the circulator 584. The circulator 584 is used to provide isolation between the forward signal and the reflected signal to facilitate accurate measurement. However, as the circulator does not provide complete isolation between its first and third ports, i.e. some of the forward signal may break through to the third port and interfere with the reflected signal, a carrier cancellation circuit may be used that injects a portion of the forward signal (from a forward coupler 582) back into the signal coming out of the third port (via injection coupler 586). The carrier cancellation circuit include a phase adjustor 598 to ensure that the injected portion is 180° out of phase with any signal that breaks through into the third port from the first port in order to cancel it out. The carrier cancellation circuit also include a signal attenuator 596 to ensure that the magnitude of the injected portion is the same as any breakthrough signal.

The reflected signal from the third port of the circulator 584 is attenuated by attenuator 588 before being input to heterodyne receiver for detection.

The heterodyne receiver is used to extract phase and magnitude information from the forward and reflected signal received from the forward coupler 580 and third port of the circulator 584. The heterodyne receiver comprises a second local oscillator 573 that outputs a signal having a frequency $f_{2LO}$ that is slightly offset from the frequency $f_2$ of the third microwave source 572. The signal output by the second local oscillator 573 is derived from a common stable reference signal, which is also communicated to the controller 560. The output signal from the second local oscillator 573 is input to amplifier 575 and then split into two separate signals by power splitter 577. These separate signals are input to respective mixers 581, 590 for mixing down the forward signal and the reflected signal from the forward coupler 580 and third port of the circulator 584. The frequency of the second local oscillator signal is selected so that the output from the mixers 581, 590 is at an intermediate frequency suitable to be received by the ADC 562 at the controller 560. As discussed below, it may be particularly advantageous for the plurality of microwave channels to generate outputs at a common intermediate frequency. The mixed down signal from each mixer 581, 590 is input to an integrated filter amplifier (e.g. comprising a band pass filter 583, 592 and amplifier 585, 594) which function to protect the second local oscillator 573 and the controller 560 from any high frequency microwave signals. The ADC 562 is configured to receive outputs D3, D4 from these filter amplifiers. Outputs D3, D4 correspond to a forward signal delivered to the instrument 516 and a reflected signal received back from the instrument 516. The instrument 516 itself is configured to contact biological tissue for the purpose of transferring the microwave EM energy into the tissue. When the instrument 516 is in contact with tissue, the forward and reflected signals can be used to determine a complex impedance of the load (biological tissue) at the distal end of the instrument.

The first and second microwave sources 518, 572 may be arranged to generate a microwave signal at any suitable frequency. However, it may be preferred for the generated frequencies to belong to one of the following ISM bands:

433.05 MHz to 434.79 MHz (1.74 MHz bandwidth with a centre frequency 433.92 MHz)

902 MHz to 928 MHz (26 MHz bandwidth with a centre frequency at 915 MHz)

2.4 GHz to 2.5 GHz (100 MHz bandwidth with centre frequency of 2.45 GHz)

5.725 GHz to 5.875 GHz (150 MHz bandwidth with a centre frequency of 5.8 GHz)

24.0 GHz to 24.25 GHz (250 MHz bandwidth with a centre frequency 24.125 MHz)

61.0 GHz to 61.5 GHz (500 MHz bandwidth with a centre frequency 61.25 GHz).

In one example, the frequency fb of first microwave source 518 is 5.8 GHz and the frequency $f_{1LO}$ of the first local oscillator 550 is 5.75 GHz. The intermediate frequency of the outputs D1, D2 is therefore 50 MHz. Meanwhile, the frequency $f_2$ of second microwave source 572 may be 2.45 GHz and the frequency $f_{2LO}$ of the second local oscillator 573 may be 2.4 GHz. In this arrangement, the intermediate frequency of the outputs D3, D4 is also 50 MHz. Thus, the ADC can receive signals having the same frequency from microwave channels that operate at the differing frequencies. Moreover, the same logic in the FPGA 564 may be used to process the signals from all of the microwave channels.

In use, the instrument 516 may be inserted through a surgical scoping device to a treatment site, whereupon the generator is activated to identify a tissue type at the distal end of the instrument. This may be done by controlling the switch 512 to connect each microwave channel to the instrument in sequence. When connected, each microwave channel is arranged to send a signal to the instrument. The controller 560 detects the forward and reflected energy, and assembles a set of complex impedances value for each frequency. The set of complex impedance values is compared with a look up table to identify the tissue type. The instrument can then be moved to a new position and the process repeated.

The position of the instrument may be controlled by a surgical robot. The position (e.g. in a predetermine coordinate system) may be communicated to the controller so that the identified tissue type can be mapped to corresponding positions at the treatment site. The controller may therefore build a map, e.g. in three dimensions, of the tissue type locations in the treatment site. The map may be used to plan a treatment phase, e.g. to identify positions in which the instrument tip is to be located to perform ablation.

In another example, a microwave channel may be provided with a microwave source and a local oscillator whose output frequencies are adjustable. In this example, a single microwave channel may be used to obtain impedance measurements at a plurality of frequencies. In addition, by monitoring the amplitude of the reflected signal as the frequency of the microwave source is swept across its range, it may be possible to identify an optimal treatment frequency, e.g. corresponding to a minimum reflected amplitude.

In yet another example, a microwave channel may be configured to determine a phase shift in the reflected signal caused by cable 515. Where the system is used with a long flexible cable, e.g. if the instrument 516 is insertable through the instrument channel of a surgical scoping device such as an endoscope, the flexing of the cable on its path to the treatment site may introduce a phase change into the conveyed forward and reflected signals. It may be desirable to identify and compensate for this phase change so that it does not introduce inaccuracy in the tissue identification process.

In order to measure a phase change introduced by the cable, the instrument 516 may be configured to include a selectively reflective element 517 which is configured as an impedance transformer that is effectively transparent to frequencies of energy for treating or measuring tissue at the tip of the instrument, while being reflective (i.e. presenting an open circuit condition) for one or more frequencies configured to detect a phase shift introduced by the cable.

The selectively reflective element 517 may be configured as any structure suitable for conveying microwave EM radiation. For example, the selectively reflective element 517 may be a coaxial transmission line, a microstrip transmission line or a hollow waveguide. The selectively reflective element 517 is configured to present a structure having an electrical length equal to a multiple half wavelength for microwave energy at frequencies intended for measurement or treatment, e.g. any of 433 MHz, 915 MHz, MHz, 2.45 GHz or 5.8 GHz. With this configuration, the selectively reflective element 517 is transparent to the microwave EM radiation, and may have an impedance selected so that it acts as an impedance transformer between the cable 515 and instrument 516. The relative permittivity $\varepsilon_r$ using in the selectively reflective element 517 may be chosen to ensure that the physical length is practical. The frequency of the microwave energy to be used in determining the phase compensation may be selected so that the selectively reflective element 517 presents a structure having an electrical length equal to an odd multiple quarter wavelength. In this scenario, the selectively reflective element 517 may effective present an open circuit condition from which a well defined reflection is obtained. The phase compensation may be obtained by the controller 560 using outputs from a heterodyne receiver configured as discussed above.

In practice, it may be desirable to use lower frequencies for treatment, and therefore the signal for determining cable phase compensation may have a higher frequency that the treatment signals. For example, in a waveguide having a relatively permittivity of 2.5, a first wavelength $\lambda_1$ at 2.45 GHz is 77.44 mm, and a second wavelength $\lambda_2$ at 13.48 GHz is 14.08 mm. These wavelengths satisfy the relation $$\frac{\lambda_1}{2} = \frac{11\lambda_2}{4}$$

which means that the selectively reflective element 517 may be configured to be transparent at 2.45 GHz and reflective at 13.48 GHz.

FIG. 5 shows a schematic diagram of a radiofrequency (RF) channel 700 with a tissue identification function that is suitable for use in an electrosurgical generator that is an embodiment of the invention. The RF channel 700 may be used in addition to the multiple microwave channels shown in FIG. 4, e.g. as an additional input to the isolator 514.

The RF channel comprises an RF signal generator 702, which may be configured with an RF frequency source and RF amplifier as described above with reference to FIG. 1. An output transformer 704 transfers a generated RF signal from the RF generator 702 on to a line for delivery to the instrument (e.g. via the isolator 514 and cable 515).

The tissue identification function is provided by component configured to measuring the actual sinusoidal voltage and current in the primary coil of the output transformer 704. A difference between the measured voltage and current is also measured to determine the phase. The voltage and current in the primary coil is related to the voltage and current in the secondary coil, which in turn is influenced by the load on the secondary circuit. When the instrument is in contact with tissue, this load is the impedance of the tissue. Assuming that the power in the primary and second circuits is the same, we have $$\frac{V_p^2}{Z_{in}} = \frac{V_s^2}{Z_t}$$

wherein $V_p$ is the voltage at the primary coil, $V_s$ is the voltage at the secondary coil, $Z_{in}$ is the input impedance of the primary circuit, and $Z_t$ is the tissue impedance (the property of interest).

Assuming $N_s \gg N_p$, we know that $$\frac{V_s}{V_p} = \frac{N_s}{N_p}$$

and hence $$\frac{Z_t}{Z_{in}} = \left(\frac{N_s}{N_p}\right)^2$$

Accordingly, measuring $Z_{in}$ can provide information about $Z_t$. The input impedance $Z_{in}$ is obtained by measuring the current $I_p$ and voltage $V_p$ in the primary circuit. In practice this is done by extracting a first voltage $V_v$ indicative of the primary voltage $V_p$, a second voltage $V_i$ indicative of primary current $I_p$, and a third voltage $V_q$ indicative of the phase difference between the primary voltage and primary current.

The first voltage $V_v$ is obtained from a potential divider 708, which taps off a detected voltage $V_d$ which is related to the primary voltage $V_p$ by the relation $$V_d = \frac{V_p R_1}{R_1 + R_2}$$

The detected voltage is conditioned by a voltage clamp 710 and buffer amplifier 716, and supplied to a comparator 722, where is compared with a reference voltage obtained from reference source 720 via buffer amplifier 718 to generate the first voltage $V_v$.

The detecting circuits for these voltages are configured as difference amplifiers, in which the output voltage corresponds to a difference between non-inverting and inverting input signals. This arrangement is used to remove any DC voltage offset and common mode noise that may otherwise corrupt the signal.

This arrangement also has the advantage of shifting the signals that are fed into the ADC to be the same amplitude. The reference voltage may be set to be between +5V and −5V. The reference source may comprise a resistor network having two fixed resistors and a potentiometer that provides the ability to tune to the required offset.

The second voltage $V_i$ is obtained from a current transformer 706 connected on the RF channel to measure the current delivered to the tissue load. The current in the second coil of the current transformer 706 is connected through a burden resistor having resistance $R_b$. The voltage $V_b$ across the burden resistor is related to the primary current $I_p$ and number of turns ($N_1$, $N_2$) in the primary and secondary coils of the current transformer 706 by the relation $$V_b = \frac{N_1}{N_2} I_p$$

The voltage $V_b$ across the burden resistor is conditioned by a voltage clamp 714 and buffer amplifier 728, and supplied to a comparator 730, where is compared with a reference voltage obtained from reference source 726 via buffer amplifier 727 to generate the second voltage $V_i$.

To derive phase information, the first voltage $V_v$ and the second voltage $V_i$ are also connected to a comparator 724 whose output is the third voltage $V_q$. This third voltage is proportional to the phase difference between the voltage and current waveforms.

The first, second and third voltages are supplied to the ADC 562 of the controller 560, which is configured in a similar way to that discussed above with reference to FIG. 4. When the instrument 516 is in contact with tissue, the first, second and third voltages can be used to determine a complex impedance of the load (biological tissue) at the distal end of the instrument.

In this example, the controller 560 includes a field-programmable gate array (FPGA) 564 that is configured to translate the first, second and third voltages into a tissue identification output signal that is communicated to a user interface 568 through a suitable connection interface 566 (e.g. Serial Peripheral Interface). The tissue identification output signal may be representative of a known tissue type, or may indicate that the instrument is in air, or may indicate that the load in contact with the instrument is unknown.

To generate the tissue identification output signal, the ADC 562 and FPGA 564 may be configured to calculate a complex impedance for the load at the instrument 516 using first, second and third voltages, then apply a calibration adjustment to the calculated complex impedance, and finally compare the calibrated complex impedance to a look up table (e.g. stored in memory 570). As mentioned above, the look up table may include information about the dielectric properties of a plurality of known tissue types, e.g. obtained from a suitable biobank such as that assembled by the Foundation for Research on Information Technologies in Society (IT'IS).

The operational amplifiers used for signal conditioning in the RF channel may preferable have a gain-bandwidth product of at least 10 MHz in order to ensure that there is a suitable margin of gain available for detected signals having a frequency of 400 kHz.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

The invention claimed is:

1. An electrosurgical generator comprising:

an electromagnetic signal supply unit for generating electromagnetic, EM, energy to be conveyed along each of a plurality of channels, wherein each of the plurality of channels is arranged to convey electromagnetic energy at a different frequency, wherein the plurality of channels includes a first channel arranged to convey electromagnetic energy at a first frequency, and a second channel arranged to convey electromagnetic energy at a second frequency that is different from the first frequency;

an output port selectively connectable to each of the plurality of channels, wherein the output port is configured to be connectable to an electrosurgical instrument for delivering the electromagnetic energy to biological tissue;

a tissue identification unit comprising a controller configured to:

detect, from each of the plurality of channels, a signal indicative of a load impedance at the output port;

detect a phase offset from energy conveyed on the second channel;

determine a set of complex impedance values from the detected signals, wherein the set of complex impedance values comprises a complex impedance value for the load at each of the first frequency and the second frequency;

apply the phase offset when determining the complex impedance value for the load at the first frequency;

identify a tissue type from the set of complex impedance values; and generate an output for communicating the identified tissue type to a user;

wherein the electrosurgical generator further comprises:

a flexible transmission line connected to the output port for conveying the electromagnetic energy to the electrosurgical instrument; and a selectively reflective element mounted at a distal end of the flexible transmission line, wherein the selectively reflective element has an electrical length that is an odd multiple quarter wavelength at the second frequency, and a multiple half wavelength at the first frequency.

2. The electrosurgical generator according to claim 1, wherein the electromagnetic signal supply unit is configured to generate microwave EM energy at a plurality of microwave frequencies, and wherein the plurality of channels comprises a plurality of microwave channels configured to convey microwave EM energy.

3. The electrosurgical generator according to claim 2, wherein the plurality of microwave frequencies include any of 433 MHz, 915 MHz, 2.45 GHZ, 3.3 GHZ, 5.8 GHz, 10 GHz, 14.5 GHZ, 24 GHz and 60 GHz.

4. The electrosurgical generator according to claim 2, wherein the tissue identification unit comprises, on each of the plurality of microwave channels:

a forward detector configured to detect a forward signal indicative of microwave EM energy travelling towards the output port; and a reverse detector configured to detect a reflected signal indicative of microwave EM energy travelling away from the output port, wherein the tissue identification unit is arranged to use the forward signal and the reflected signal detected on each of the plurality of microwave channels as the signal indicative of the load impedance at the output port for that microwave channel.

5. The electrosurgical generator according to claim 4, wherein the tissue identification unit comprises, for each of the plurality of microwave channels, a heterodyne receiver configured to:

receive the forward signal and the reflected signal as inputs;

receive a reference signal having a frequency offset from a frequency of the forward signal and the reflected signal; and generate a forward detection signal and a reflected detection signal that have an intermediate frequency obtained by mixing down the forward signal and the reflected signal with the reference signal.

6. The electrosurgical generator according to claim 5, wherein the set of complex impedance values comprises a complex impedance value for the load at each of the plurality of microwave frequencies, wherein the controller is arranged to receive and digitise the forward detection signal and the reflected detection signal for each of the plurality of microwave channels, and calculate the complex impedance value for the load at each of the plurality of microwave frequencies using a corresponding digitised forward detection signal and reflected detection signal.

7. The electrosurgical generator according to claim 6, wherein the controller includes a field-programmable gate array configured to calculate the complex impedance value for the load at each of the plurality of microwave frequencies.

8. The electrosurgical generator according to claim 5, wherein the reference signal for each of the plurality of microwave channels is selected to cause all forward detection signals and reflected detection signals for each of the plurality of microwave channels to have a same intermediate frequency.

9. The electrosurgical generator according to claim 8, wherein the intermediate frequency is equal to or less than 100 MHz.

10. The electrosurgical generator according to claim 1, wherein the electromagnetic signal supply unit is configured to generate radiofrequency, RF, EM energy, and wherein the plurality of channels comprises an RF channel configured to convey the RF EM energy.

11. The electrosurgical generator according to claim 10, wherein the RF EM energy has a frequency equal to or less than 400 MHz.

12. The electrosurgical generator according to claim 10, wherein the RF channel is coupled to the output port through an output transformer, and wherein the tissue identification unit comprises, on the RF channel:

a current transformer configured to determine a signal indicative of current in a primary coil of the output transformer;

a voltage divider configured to determine a signal indicative of voltage across the primary coil of the output transformer; and a comparator configured to determine a signal indicative of a phase difference between the voltage across and current in the output transformer, wherein the tissue identification unit is arranged to use the signals indicative of voltage, current and phase difference as the signal indicative of the load impedance at the output port for the RF channel.

13. The electrosurgical generator according to claim 12, wherein the set of complex impedance values comprises a complex impedance value for the load at the RF channel, wherein the controller is arranged to receive and digitise the signals indicative of voltage, current and phase difference, and calculate the complex impedance value for the load at the RF channel using the digitised signals.

14. The electrosurgical generator according to claim 13, wherein the controller includes a field-programmable gate array configured to calculate the complex impedance value for the load at the RF channel.

15. The electrosurgical generator according to claim 1, wherein the controller is configured to apply a calibration adjustment when determining the set of complex impedance values from the detected signals.

16. The electrosurgical generator according to claim 1, wherein the electromagnetic signal supply unit is configured to generate microwave EM energy for tissue ablation, and convey the microwave EM energy for tissue ablation to the output port along a dedicated channel that is independent of the tissue identification unit.

17. The electrosurgical generator according to claim 16, wherein the controller is configured to generate the output for communicating the identified tissue type upon determining a match between more than one complex impedance value in the set of complex impedance values and known complex impedances at corresponding frequencies.

18. The electrosurgical generator according to claim 1, wherein the controller includes a memory storing a look up table that contains known complex impedances for a plurality of tissues types at different frequencies, and wherein the controller is configured to identify the tissue type by comparing the set of complex impedance values to the known complex impedances.

19. The electrosurgical generator according to claim 1, wherein the identified tissue type is any of: tumour tissue; an air-filled volume; a mucus-filled volume; muscle; lung; fat; liver; brain; or ablated biological material.

20. The electrosurgical generator according to claim 1, wherein the controller is configured to detect a boundary between two different tissue types.

21. The electrosurgical generator according to claim 20, wherein the boundary is any one of:

(a) a boundary between non-ablated non-cancerous biological tissue and non-ablated tumour tissue;

(b) a boundary between non-ablated tumour tissue and ablated biological tissue; or (c) a boundary between non-ablated non-cancerous biological tissue and ablated biological tissue.

\* \* \* \* \*